US010238546B2

(12) United States Patent
Bernier et al.

(10) Patent No.: US 10,238,546 B2
(45) Date of Patent: Mar. 26, 2019

(54) ACTIVE HEARING PROTECTION DEVICE AND METHOD THEREFORE

(71) Applicant: EERS GLOBAL TECHNOLOGIES INC., Montréal (CA)

(72) Inventors: Antoine Bernier, Montréal (CA); Jérémie Voix, Montréal (CA)

(73) Assignee: EERS GLOBAL TECHNOLOGIES INC., Montreal QC (CA)

( * ) Notice: Subject to any disclaimer, the term of this patent is extended or adjusted under 35 U.S.C. 154(b) by 0 days.

(21) Appl. No.: 15/545,908

(22) PCT Filed: Jan. 22, 2016

(86) PCT No.: PCT/CA2016/000019
§ 371 (c)(1),
(2) Date: Jul. 24, 2017

(87) PCT Pub. No.: WO2016/115622
PCT Pub. Date: Jul. 28, 2016

(65) Prior Publication Data
US 2018/0021176 A1      Jan. 25, 2018

Related U.S. Application Data

(60) Provisional application No. 62/106,397, filed on Jan. 22, 2015.

(51) Int. Cl.
*A61F 11/14* (2006.01)
*H04R 3/04* (2006.01)
*H04R 1/04* (2006.01)
*H04R 1/10* (2006.01)

(52) U.S. Cl.
CPC .............. *A61F 11/14* (2013.01); *H04R 1/04* (2013.01); *H04R 1/1016* (2013.01); *H04R 1/1083* (2013.01); *H04R 3/04* (2013.01); *A61F 2011/145* (2013.01); *H04R 2410/05* (2013.01);
(Continued)

(58) Field of Classification Search
None
See application file for complete search history.

(56) References Cited

U.S. PATENT DOCUMENTS

| 5,825,894 A | 10/1998 | Shennib |
| 5,923,764 A | 7/1999 | Shennib |
| 6,167,138 A | 12/2000 | Shennib |

(Continued)

*Primary Examiner* — Curtis A Kuntz
*Assistant Examiner* — Qin Zhu
(74) *Attorney, Agent, or Firm* — Praxis

(57) ABSTRACT

An earpiece adapts to the acoustics characteristics and needs of its user to provide a perceptually transparent hearing protection, apart from uniform loudness reduction. An occlusion effect (OE) active noise control (ANC) system reduces the augmented perception of one's own voice while occluded. This occlusion effect active control adapts to the specific acoustic characteristics of the user to provided better control of the details occlusion effect reduction, and enhanced performances relative to fixed or one-size-fits-all solutions. An isolation effect (IE) filtering algorithm adapts itself to the user's acoustic characteristics to provide a uniform attenuation either in dB or in phons. Additionally, the device may be used as an in-ear monitor that also adapts to its user characteristics to provide in-ear quality sound.

22 Claims, 8 Drawing Sheets

(52) U.S. Cl.
CPC ...... *H04R 2420/09* (2013.01); *H04R 2460/09* (2013.01)

(56) References Cited

U.S. PATENT DOCUMENTS

| | | | |
|---|---|---|---|
| 6,937,738 B2 | 8/2005 | Armstrong et al. | |
| 7,433,481 B2 | 10/2008 | Armstrong et al. | |
| 7,477,754 B2 | 1/2009 | Rasmussen et al. | |
| 7,590,254 B2 | 9/2009 | Olsen | |
| 2005/0254665 A1* | 11/2005 | Vaudrey | G10K 11/1788 381/72 |
| 2007/0189569 A1* | 8/2007 | Haapapuro | H04R 1/1016 381/380 |
| 2010/0119077 A1* | 5/2010 | Platz | A61F 11/08 381/72 |
| 2011/0274284 A1 | 11/2011 | Mülder et al. | |
| 2012/0057734 A1* | 3/2012 | Ambrose | F04B 45/04 381/328 |
| 2012/0076334 A1* | 3/2012 | Anderson | H04R 25/505 381/317 |
| 2014/0126734 A1* | 5/2014 | Gauger, Jr. | H04R 3/002 381/71.6 |
| 2014/0146989 A1* | 5/2014 | Goldstein | A61F 11/08 381/380 |
| 2014/0153768 A1* | 6/2014 | Hagen | H04R 1/1008 381/380 |
| 2015/0063612 A1 | 3/2015 | Petersen et al. | |

* cited by examiner

Plant response, from LS input to IEM output

ACTIVE HEARING PROTECTION DEVICE AND METHOD THEREFORE

CROSS-REFERENCE TO RELATED APPLICATIONS

This is a U.S. national phase entry of PCT application No. PCT/CA2016/000019 filed on Jan. 22, 2016, and benefit of U.S. Provisional Application for Patent Ser. No. 62/106,397 filed on Jan. 22, 2015, being incorporated herein by reference, is hereby claimed.

FIELD OF THE INVENTION

The present invention relates to hearing protection and hearing aid devices, and more specifically to an active hearing protection device and method therefore, especially for use by musicians and the like.

BACKGROUND OF THE INVENTION

Musicians are noise-exposed workers who heavily rely on their auditory sense and should protect it by wearing hearing protectors. However, many musicians do not protect their hearing because they find that the use of hearing protectors is detrimental to their performance, as they cause perceptual discomfort.

Professional musicians are exposed to high levels of sound and should protect their hearing to avoid permanent hearing loss that could compromise their career. Since high sound pressure levels are often required by a musician's work, the logical solution would be to wear hearing protection devices (HPDs) when required. However, perceptual discomfort associated with wearing HPDs can discourage musicians from using them. This perceptual discomfort is caused by two detrimental effects: the occlusion effect (OE) and the isolation effect (IE).

The occlusion effect (OE) is often reported as an unnatural and annoying perception of one's own voice or, instrument coupled to the skill, when wearing HPDs.

The isolation effects regroups acoustical and psychoacoustical factors that causes hearing protection users to experience perception shifts that an ideal hearing protection should not cause, making them feel isolated from their sound environment.

The isolation and occlusion effects are highly unfavorable to the musicians' auditory perception and compromise their capacity to perform to the best of their abilities for their audience. The isolation effect can make it difficult for musicians to judge the sound quality that is being presented to their audience. When, as a consequence of the occlusion effect, an augmented and unnatural perception of one's own voice or instrument is predominantly what is heard, musicians cannot hear the subtle cues that they depend on to adjust their playing. Cues such as knowing how their timbre blends with their colleague's or how loudly their instrument sounds and resonates in a given space can potentially make a big difference in one's performance. These adverse effects are causing some musicians to decide not to wear HPDs.

Oticon A/S™ method for counteracting the occlusion effects described in U.S. Pat. No. 7,477,754 dated Jan. 13, 2009 is based on a generic fixed feedback controller with limited performance in terms of active control gain, because it does not account for wide inter-user variability, and therefore must make compromises regarding performance in order to be stable on all users, in various conditions. While such fixed feedback controller may be sufficient for hearing aid applications, where the external audio feed is played back at a sufficiently high level that partially masks the residual occlusion effect to reduce discomfort, it is in practice insufficient for other in-ear devices such as musicians earplugs or communication devices where a re-establishment of open-ear conditions would be desired.

Phonak AG™'s system and method for providing active hearing protection to a user described in US Patent Publication No:2011/0274284 A1 published on Nov. 10, 2011 features frequency band adjustments to correct the audio response of an in-ear device based on equal loudness across frequencies. The gain adjustments are limited in terms of frequency resolution, since they are limited to specific audio bands, and the gain factors are a function of a target loudness reduction that is selected by the wearer. With no means of assessing the true attenuation that is experienced by the user, which can vary greatly across users, these corrections cannot completely solve the isolation effect. These two limiting factors certainty affect the quality and usefulness of such device in hearing protection applications.

The occlusion effect (OE) is often reported as an unnatural and annoying perception of one's own voice when wearing HPDs. It will affect all musicians whose instrument induces vibrations to the skull, including singers and musicians whose instrument is pressed against any part of the head, such as a trumpet or violin. Although there is a direct solid borne sound path to the cochlea, it is generally accepted that the main objective occlusion effect is due to the existence of another solid borne sound path that ultimately reaches the cochlea by sound generation due to the vibrations of the ear canal walls that cause pressure fluctuations in the air contained in the ear canal. When the ear canal is unoccluded, less energy is transferred to the ear canal by bone conduction as the ear canal has an open-end, hence a lower acoustic impedance, and what is heard is predominantly the sound wave arriving from the air conduction path between the source (e.g. vocal tract) and the ear. However, when the ear canal is occluded, the walls have a strong coupling with the cavity and thus the ear canal sound level is greater and is picked up by the auditory system while the air conduction path is blocked, so what is heard is predominantly the sound wave traveling by bone conduction. Since this effect is more pronounced at low frequencies, below 1000 Hz, the result is an augmented and unnaturally "boomy" perception of one's own voice. FIG. 1 illustrates how the occlusion effect occurs.

It is apparent from FIG. 2 that the sound pressure level (SPL) increase caused by occlusion effect occurs in the lower frequencies of the speech bandwidth. The SPL in the occluded ear canal when one is speaking can typically amounts to 90 to 100 dB(SPL), and the occlusion effect results in an amplification of the low frequencies of the talker's own voice by up to 20 to 30 dB.

Occluding the ear with a HPD has an inherent effect on a wearer's auditory perception on multiple levels. The isolation effect (IE) regroups phenomena that cause a perception shift and/or a feeling of being isolated from a given sound environment. It originates from many causes: the different acoustical behavior of an open vs an occluded ear, the attenuation provided by typical HPDs, the impact of loudness perception on the perceived attenuation, and the fixed attenuation of most hearing protectors, sometimes resulting in over-attenuation.

The open, or unoccluded ear canal exhibits a wide acoustic resonance around 2.7 kHz, although the center frequency varies greatly among individuals. This resonance helps understanding speech consonants, which are mostly in this frequency region, and is a natural part of the way that we hear. Unfortunately, occluding the ear canal changes its acoustic properties and shifts the resonance to higher frequencies, to around 5.5 Hz and 8 kHz, as it is dependent on the remaining volume of the ear canal and its specific attributes. The shifting of this important resonance has two consequences, the first one is that a loss in sensitivity is felt where the natural ear resonance is supposed to occur, even without considering the attenuation of the earplug. The second consequence is that an increase in sensitivity is felt where the resonance of the occluded ear canal now is. Both consequences cause an unnatural perception shift.

Occluding the ear with a HPD typically results in an unbalanced attenuation, much more pronounced in the high frequencies than in the low frequencies. One reason for the low attenuation at low frequencies is that the earplug is free to vibrate because of its own flexibility as well as the flexibility of the ear canal flesh. This phenomenon is not significant at high frequencies, and a more pronounced attenuation is often seen, accentuated by the fact that occluding the ear shifts its natural resonance. Very small leaks between the device and the ear canal can also cause lower low frequency attenuation.

FIG. 3 shows typical shapes of non-uniform attenuation provided by an earplug-type HPD, an earmuff-type HPD, and both devices worn together, as well as the maximum attenuation limit of HPDs. This limit is imposed by the fact that sounds can bypass the HPD by bone and tissue conduction to the inner ear.

Loudness is defined as the perceived magnitude of a sound. it is a psychophysical magnitude strongly correlated to the physical magnitude of sound pressure level: one does not directly feel sound pressure level, one feels a loudness sensation caused by sound pressure level. Since loudness is frequency and SPL dependent, but in a non-linear way, a uniform decrease in SPL at all frequencies composing a sound does not usually translate to a uniform decrease in loudness at all frequencies of the sound. According to loudness models, if one was to wear perfectly uniform attenuation earplugs and another was hearing naturally, in the same given sound environment, they could feel different spectral balances: the relative difference in loudness between the frequency components would not be the same. This is analogous to what happens to perceived spectral balance as the volume of an audio material is turned up or down. In contrast, if a given earplug was not necessarily uniform in dB of attenuation, but was capable of producing uniformly decreasing loudness over the audio bandwidth, wearing or removing them would not have any effect on the perceived spectral balance. Since spectral balance assessment is used by musicians to blend their instruments together, adjust their playing, and even assess timbre, it is possible that the non-linearity of loudness perception is detrimental to the acceptance of uniform attenuation HPDs.

Accordingly, there is a need for an improved active hearing protection device and method therefore.

SUMMARY OF THE INVENTION

It is therefore a general object of the present invention to provide an improved active hearing protection device and method therefore, that substantially solve the above-mentioned problems and drawbacks.

An advantage of the present invention is that the active hearing protection device and method therefore address the issue raised by U.S. Pat. No. 7,477,754 and offer a customized feedback controller that adapts to its users acoustic characteristics, offering better performance than a fixed controller could since it is bound to compromise between several users.

Another advantage of the present invention is that the active hearing protection device and method therefore address both issues raised by US Patent Publication No:2011/0274284 A1, with a digital filter, running on the full audio spectrum bandwidth (rather than on a limited set of frequency bands) to implement loudness correction.

Yet another advantage of the present invention is that it adapts to its user to provide a more uniform attenuation than HPD of which the acoustics have not been customized to the user, by implementing, in-situ, individual corrections in the frequency response of the in-ear electronic earplug. These individual frequency response corrections account for the specific occluded ear canal resonance of the user and mimic the open ear canal transfer function so that the received audio signal sound as natural as it is with open ears. This implies the use of an in-ear microphone to monitor the residual signal under the protector, and outer-ear microphone to monitor the sound environment, as well as a model of the acoustic characteristics of the user's occluded ear canal, to account for the differences between what is monitored at the in-ear microphone, and what is present at the eardrum, at the other end of the ear canal.

A further advantage of the present invention is that it does not over-attenuate the signal by providing a variable uniform attenuation that can adapt to the environment in which the user is, or to the user command.

Another advantage of the present invention is that it makes it possible to have two users with different acoustic characteristics experience very similar levels of OE active cancelation or IE correction that allows for perceptual research that was previously difficult, because a same device under test would provide a wide range of performance depending on the acoustic characteristics of the user.

Yet a further advantage of the present invention is that it allows a user to provide some user inputs to the controller to selectively modify the processed signal, and optimized for acoustic transparency and neutrality, while offering to take into account individual preferences of the user.

According to an aspect of the present invention there is provided a hearing protection device for protecting an ear of a user while reducing an occlusion effect and/or an isolation effect induced by the hearing protection device, the device comprising:

an earpiece adapted to be located into the ear for occluding an ear canal of the ear, said earpiece having an inner-ear microphone (IEM) adapted to be in fluid communication with the occluded ear canal, an outer-ear microphone (OEM) adapted to be in fluid communication with an adjacent environment outside the ear, and a receiver adapted to be in fluid communication with the occluded ear canal; and a controller connecting to the inner-ear microphone (IEM) to receive an internal signal therefrom over a predetermined frequency range and to the outer-ear microphone (OEM) to receive an external signal therefrom over the predetermined frequency range, said controller digitally actively processing the internal and external signals taking into account individual acoustic characteristics of the occluded ear canal and sending a processed signal to the receiver, the processed signal and the internal signal producing an actual signal having an actual sound pressure level distribution being substantially uniformly attenuated over the predetermined frequency range relative to a corresponding virtual sound pressure level distribution of a virtual signal that would be heard by the ear of the user with an non-occluded ear (or without the earpiece), the actual signal compensating for occlusion (OE) and isolation (IE) effects of the earpiece.

In one embodiment, the controller includes:

for accounting of the occlusion effect of the earpiece, an OE compensator digitally compensating the internal signal toward a target performance (signal gain over frequency range) signal curve into an OE compensated signal using the individual acoustic characteristics and an acoustic plant response model including the inner-ear microphone and the receiver, the target performance (signal gain over frequency range) signal curve being derived from at least one of a pre-defined performance signal curve and a monitoring of an OE induced signal; and for accounting of the isolation effect of the earpiece, an IE filter digitally filtering the external signal toward a target system frequency response (loudness) signal curve into an IE filtered signal using the individual acoustic characteristics and an acoustic system response model including the inner-ear and outer-ear microphones and the receiver, the target system frequency response (loudness) signal curve being derived from at least one of a pre-defined loudness model curve and a pre-defined passive attenuation signal curve of the earpiece;

wherein the controller sending the processed signal combining the OE compensated and IE filtered signals to the receiver.

In one embodiment, the device further includes a user input item adapted for receiving a first input from the user and connecting to the controller, wherein the target performance (signal gain over frequency range) signal curve being derived from at least one of the pre-defined performance signal curve, the monitoring of the OE induced signal, and the first input Conveniently, the user input item is adapted for receiving a second input from the user, the target system frequency response (loudness) signal curve being derived from at least one of the pre-defined loudness model curve, the pre-defined passive attenuation signal curve of the earpiece, and the second input.

In one embodiment, the controller ensures a minimum phase shift of the processed signal relative to the internal signal, and allows maximum gain and phase margins of the processed signal using the first and second inputs from the user.

In one embodiment, the device further includes an auxiliary port connecting to the controller and for receiving an auxiliary signal therein to be transmitted to the receiver, and wherein, for accounting of an impact of the auxiliary signal on the actual signal, the controller further includes an auxiliary filter digitally filtering the external signal toward a target auxiliary frequency response (loudness) signal curve into an auxiliary adjusted signal using the individual acoustic characteristics and an acoustic plant response model, the target auxiliary frequency response (loudness) signal curve being derived from a pre-defined auxiliary target curve, and wherein the controller sending the processed signal combining the OE compensated, IE filtered and auxiliary adjusted signals to the receiver.

In one embodiment, the user input item is adapted for receiving a third input from the user, the target frequency response (loudness) signal curve being derived from at least one of the pre-defined auxiliary target curve and the third input.

Conveniently, the first input from the user is a first tuning factor of an amplitude and/or frequency of the compensated signal so as to allow the user to select a desired amplitude and/or frequency thereof; the second input from the user is an attenuation level of the filtered signal so as to allow the user to select a desired attenuation thereof; and the third input from the user is an auxiliary attenuation level of the auxiliary adjusted signal so as to allow the user to select a desired attenuation thereof.

In one embodiment, at least one of the individual acoustic characteristics and the passive attenuation signal curve of the earpiece being determined from the internal and external signals measured under a plurality of pre-determined test sound environment signals.

In one embodiment, at least one of the target performance signal curve and the target system frequency response signal curve is actively modified depending on at least one of the individual acoustic characteristics, the acoustic plant response model, and the acoustic system response model.

In one embodiment, at least one of the target performance signal curve, the target system frequency response signal curve, and the target auxiliary frequency response signal curve is actively modified depending on at least one of the individual acoustic characteristics, the acoustic plant response model, and the acoustic system response model.

According to another aspect of the present invention there is provided a method for reducing acoustic occlusion (OE) and/or isolation (IE) effects induced by an earpiece located into an ear of a user and occluding an ear canal of the ear, the earpiece having an inner-ear microphone (IEM) adapted to be in fluid communication with the occluded ear canal, an outer-ear microphone (OEM) adapted to be in fluid communication with an adjacent environment outside the ear, and a receiver adapted to be in fluid communication with the occluded ear canal, a controller connects to the internal and outer ear microphones and to the receiver, the method comprising the step of:

actively reducing acoustic occlusion (OE) and/or isolation (IE) effects induced by the earpiece located into the occluded ear canal using the controller sending a actively processed signal to the receiver based on signals received by the internal (IEM) and outer (OEM) ear microphones over a predetermined frequency range and taking into account individual acoustic characteristics of the occluded ear canal, the actively processed signal and the internal signal producing an actual signal having an actual sound pressure level distribution being substantially uniformly attenuated over the predetermined frequency range relative to a corresponding virtual sound pressure level distribution of a virtual signal that would be heard by the ear of the user with an non-occluded ear (or without the earpiece), the actual signal compensating for occlusion (OE) and isolation (IE) effects of the earpiece.

In one embodiment, the step of actively reducing includes actively controlling the occlusion effect (OE) from the earpiece and actively compensating for the isolation effect (IE) induced by the earpiece.

In one embodiment, the controller includes an OE compensator and an IE filter, and wherein the step of actively controlling includes the steps of:

using the OE compensator for accounting of the occlusion effect of the earpiece, digitally compensating the internal signal toward a target performance (signal gain over frequency range) signal curve into an OE compensated signal using the individual acoustic characteristics and an acoustic plant response model including the inner-ear microphone and the receiver, the target performance (signal gain over frequency range) signal curve being derived from at least one of a pre-defined performance signal curve and a monitoring of an OE induced signal; and using the IE filter for accounting of the isolation effect of the earpiece, digitally filtering the external signal toward a target system frequency response (loudness) signal curve into an IE filtered signal using the individual acoustic characteristics and an acoustic system response model including the inner-ear and outer-ear microphones and the receiver, the target system frequency response (loudness) signal curve being derived from at least one of a pre-defined loudness model curve and a pre-defined passive attenuation signal curve of the earpiece; the controller sending the processed signal combining the OE compensated and IE filtered signals to the receiver.

In one embodiment, at least one of the target performance signal curve and the target system frequency response signal curve is actively modified depending on at least one of the individual acoustic characteristics, the acoustic plant response model, and the acoustic system response model.

In one embodiment, an auxiliary port for receiving an auxiliary signal therein to be transmitted to the receiver connects to the controller, and wherein the step of actively controlling includes the step of:

using the auxiliary filter for accounting of an impact of the auxiliary signal on the actual signal, the controller further includes an auxiliary filter digitally filtering the external signal toward a target auxiliary frequency response (loudness) signal curve into an auxiliary adjusted, signal using the individual acoustic characteristics and an acoustic plant response model, the target auxiliary frequency response (loudness) signal curve being derived from a pre-defined auxiliary target curve; the controller sending the processed signal combining the OE compensated, IE filtered and auxiliary adjusted signals to the receiver.

In one embodiment, at least one of the target performance signal curve, the target system frequency response signal curve, and the target auxiliary frequency response signal curve is actively modified depending on at least one of the individual acoustic characteristics, the acoustic plant response model, and the acoustic system response model.

In one embodiment, a user input item adapted for receiving at least one input from the user connects to the controller, and wherein at least one of the target performance signal curve, the target system frequency response signal curve, and the target auxiliary frequency response signal curve is further derived from the at least one input.

Conveniently, the step of actively controlling includes the step of: ensuring a minimum phase shift of the processed signal relative to the internal signal, and allowing maximum gain and phase margins of the processed signal using the at least one input from the user.

In one embodiment, the method further includes, before the step of actively controlling, the step of: determining at least one of the individual acoustic characteristics and the passive attenuation signal curve of the earpiece from the internal and external signals measured under a plurality of pre-determined test sound environment signals.

Other objects and advantages of the present invention will become apparent from a careful reading of the detailed description provided herein, with appropriate reference to the accompanying drawings.

BRIEF DESCRIPTION OF THE DRAWINGS

Further aspects and advantages of the present invention will become better understood with reference to the description in association with the following Figures, in which similar references used in different Figures denote similar components, wherein.

DETAILED DESCRIPTION OF THE INVENTION

Figure 1:
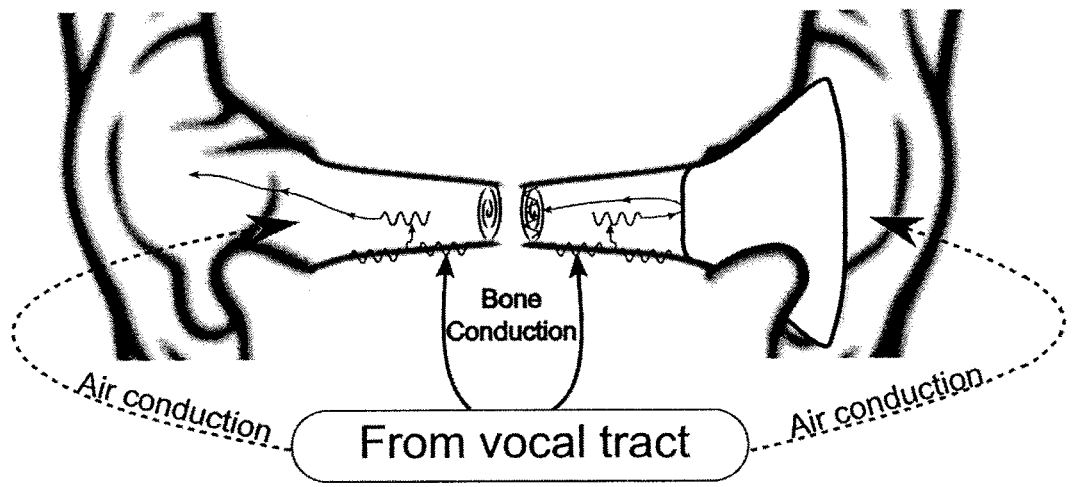
FIG. 1 is a schematic view of the prior art showing the cause of the occlusion effect in which the air conduction path prevails, and bone conduction path prevails, leading to an unnatural and augmented perception of one's own voice.
Figure 2:
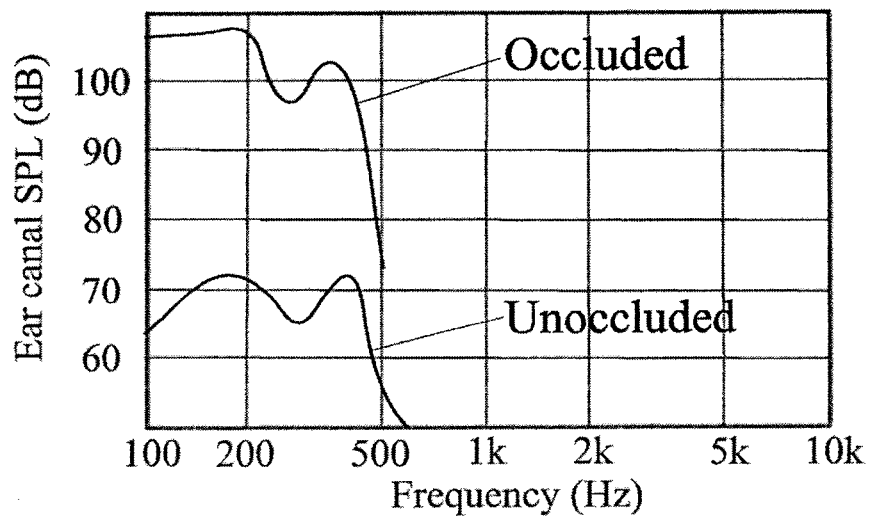
FIG. 2 is a schematic diagram of the prior art showing a sound pressure level (SPL) in an unoccluded ear canal and an occluded ear canal when a subject is vocalizing.
Figure 3:
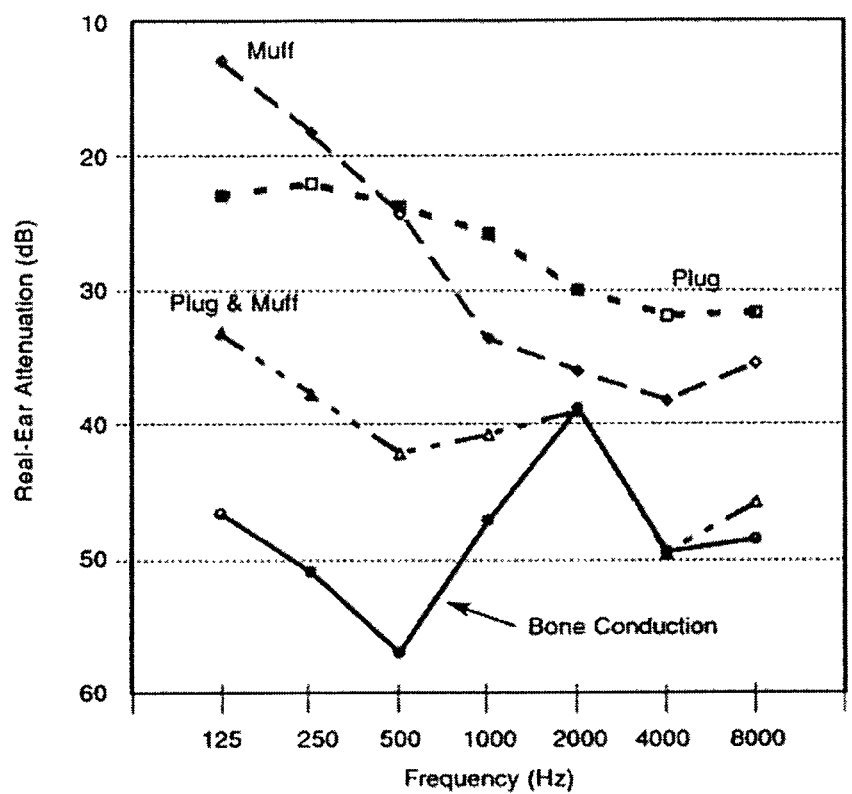
FIG. 3 is a schematic plot diagram of the prior art showing Bone-conduction limits to HPD attenuation and an example of the attenuation provided by an earplug, an earmuff, and the two devices worn together.

With reference to the annexed drawings the preferred embodiment of the present invention will be herein described for indicative purpose and by no means as of limitation.

As a solution to the above-mentioned effects, a HPD (hearing protection device) 20 incorporating active noise control of the occlusion effect (OE) and compensation algorithms to the isolation effect (IE) in accordance with an embodiment of the present invention is needed. Furthermore, it is required that such a HPD 20 adapts to its user.

The OE and IE actually experienced can vary greatly across users and is largely dependent on their individual acoustic characteristics 40, which is an umbrella term for factors including but not limited to: the shape of their external ears including the ear canal 10 and the acoustical properties of their open and occluded ear canal, dependent on its shape, length, stiffness, eardrum 12 impedance.

Since the different acoustic characteristics across users cause significant variation of the passive attenuation 36 of the HPD, the internal loudspeaker frequency response, the SPL distribution at the eardrum 12, the performance of any in-ear active noise control system or correction scheme, and the fact that these can all vary even when a single user inserts the same device multiple times in the ear canal, customization, or adaptation to its user, of a HPD 20 incorporating OE and/or IE compensation is required. Given all these variables, a fixed OE or IE active solution could potentially make things worse than if it was not included.

For example, regarding the IE, even if an earpiece, such as an earplug or the like, provides a uniform attenuation on average, a great inter-user variability is commonly observed due to the ear canal acoustic properties and the acoustic seal between the earplug and the ear canal. This means that even if the earplug offers uniform attenuation on average, in practice it is possible that no individual actually gets the advertised uniform attenuation. A way to correct for this inter-user variability as well as an inter-insertion variability is needed if the HPD is to offer a controlled attenuation.

Furthermore, the details of the "optimal" solution are complex to define for both the OE and IE. For instance. an average occlusion effect reduction that would provide sufficient perceptual results is yet to be quantified, and the frequency response of the attenuation that musicians would truly want needs to be verified. To accurately answer these questions, perceptual tests are required. However, for such tests to be accurate, a method of controlling the wide inter-user variability is mandatory. This is another motivation to adapt the HPD to the user specific acoustic characteristics, as it would permit to offer controlled performance not only across users but also for one user on each test or usage session.

In addition to the specific acoustic characteristics of its user, it is beneficial that the system adapts to its user's preferences for both IE and OE solutions. While customized correction schemes based on sound acoustic and psychoacoustic theory offer good results, the user might have specific preferences that could come, for instance, from personal tastes but also from individual condition that are not part of his acoustics characteristics as defined in this document, such as hearing loss.

An additional concern for OE active control is that since it is adjusted to offer optimal performance around a particular frequency or limited bandwidth, it is important to choose that frequency according to the intended use. For example, a man's voice may cause most of the energy resulting from occlusion effect to be around 150-200 Hz, while a woman's voice may shift that energy to around 300 Hz, and a flute might cause the most occlusion effect around 500 Hz. It is even probable that some musicians seldom play any note as low as 250 Hz, such as a trumpeter or a flutist In that case, aiming for a maximum occlusion effect reduction at this frequency could be inadequate.

An advantage of the present invention is that the active hearing protection device and method therefore allow for the automatic customization of an active HPD 20 for a user (such as a musician for example) to the user's characteristics and needs, by adapting the reduction of the isolation and/or occlusion effect to the user.

This customization is possible through measurements using the inner-ear microphone (IEM) 24 and/or the outer-ear microphone (OEM) 26 and/or the loudspeaker (LS) 28 or receiver, all mounted onto the earplug 22 of the device 20.

It can be enhanced through the estimation of an ear canal model from the available related information provided by the IEM 24 allowing in-situ measurement of the loudspeaker (LS) 28 response in any ear canal. By comparing the actual response of the LS 28 to a previously developed LS source model, it is possible to assess how the ear canal 10 and eardrum 12 loads interact with the source (the loudspeaker) to deduct occluded ear canal information. This allows estimation of how the sound from the IEM 24 to the eardrum will be modified, and to correct accordingly to be in greater control of what the user hears and to deduct and emulate the acoustics of his unoccluded (non-occluded or open) ear canal 10, with the main difference being lower SPL, resulting in uniform attenuation. This further allows to provide an occlusion effect active control that is tuned to the user and provides the best possible performance and stability in any specific ear, given the limits of the system.

Figure 4:
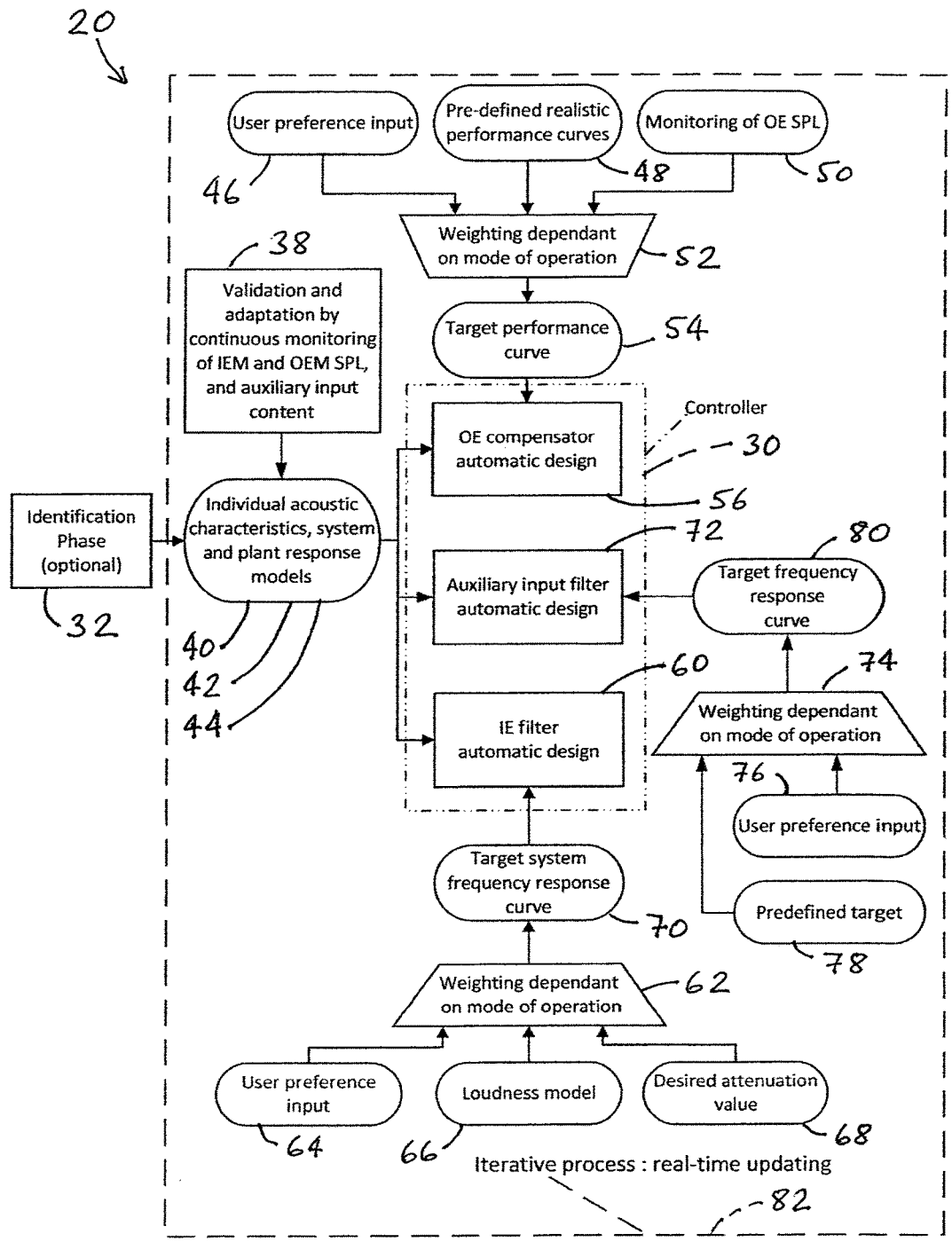
FIG. 4 is a schematic representation of variables used in the design process of the controller of an active hearing protection device, and method therefore, in accordance with an embodiment of the present invention.

The method for typically customizing up to three correction algorithms, together forming the controller 30, is shown on FIG. 4. In one embodiment of the invention, upon insertion of the HPD 20, a preliminary identification phase 32 can be triggered, where the device uses test signals to gather information about the acoustics characteristics 40 of the user and their effect on the earplug resulting acoustics. In another embodiment, as represented by item 38, these information are gathered continuously in real-time, using information provided by the IEM 24 and/or OEM 26, and optionally auxiliary input content 34, if present, and are either used to update the information gathered in the identification phase 32, or to start building models of the acoustic characteristics 40 if no identification phase was performed.

In one embodiment of the invention, a weighting 52 is done between user preference first input 46 and/or pre-defined realistic performance curves 48 and/or monitoring of OE induced SPL 50 using the IEM 24 and/or OEM 26 to output a target performance curve 54 of the OE active control. An automatic design algorithm uses this target performance curve 54 , as well as models 42, 44 and measurement representing acoustics characteristics 40 of the user and their effect on the earplug resulting acoustics, along with pre-defined design constraints to output a customized OE compensator 56.

In another embodiment of the invention, a similar process is used to automatically design a customized IE filter 60. A weighting 62 is performed between user preference second input 64 and/or a loudness model 66 and/or a target attenuation shape or overall value 68 that can be the result of an automatic algorithm proposing a safe attenuation, to output a target system frequency response curve 70. An automatic design algorithm uses this target frequency response curve 70, well as models 42, 44 and measurement representing acoustics characteristics 40 of the user and their effect on the earplug resulting acoustics and passive 36 and active attenuation, along with pre-defined design constraints to output the customized IE filter 60.

In another embodiment of the invention, a similar process is used to automatically design a customized auxiliary input filter 72. An auxiliary input 34 is an input that allows to connect an audio electrical signal that is meant to be acoustically reproduced inside the ear, such as music or the like, through the LS 28. A weighting 74 is performed between user preference third input 76 and/or a predefined target 78, to output a target frequency response curve 80. An automatic design algorithm uses this target frequency response curve 80, as well as models 42, 44 and measurement representing acoustics characteristics 40 of the user and their effect on the earplug resulting acoustics, along with pre-defined design constraints to output a customized auxiliary input filter 72.

In one embodiment, these processes are iterative 82 and may be changed and updated in real-time for up to three correction algorithms, together forming the controller 30. In another embodiment, a single off-line phase is triggered and uses an identification phase 32 to gather the required information before automatically designing up to three correction algorithms, together forming parts of the controller 30.

Figure 8:
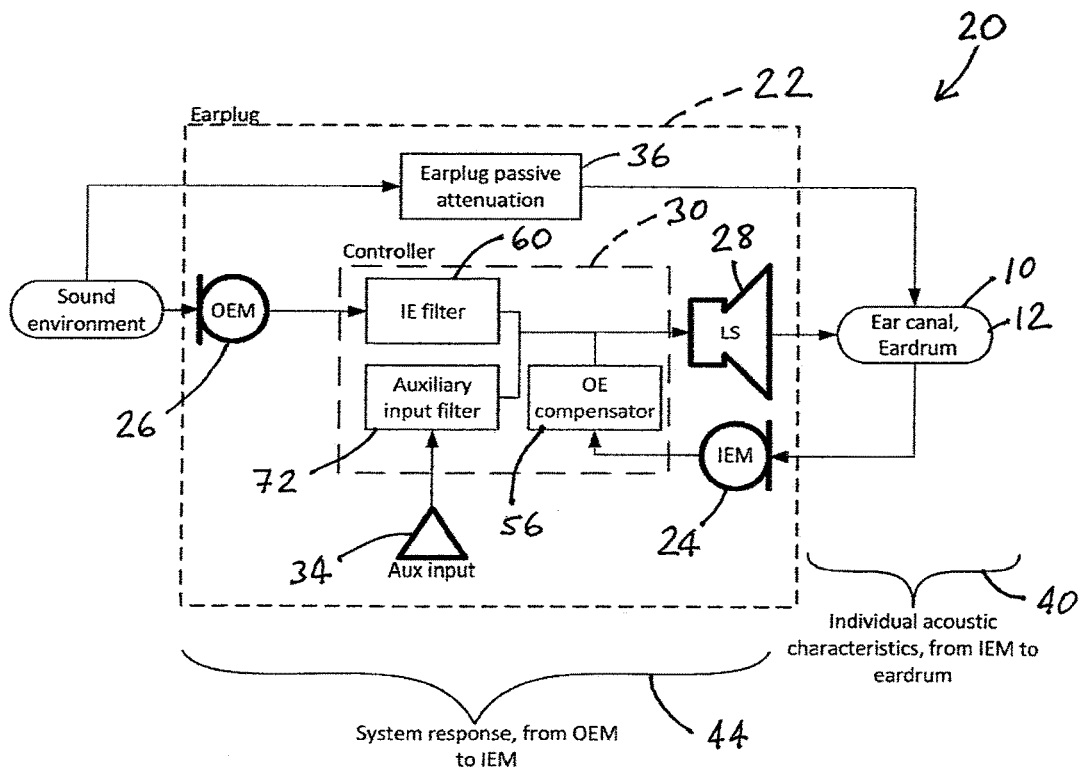
FIG. 8 is a schematic architecture diagram representation of the signal paths of the complete system of the present invention.

FIG. 8 shows the signal path including the controller 30 and how the various elements are connected.

Addressing the Occlusion Effect

Figure 5:
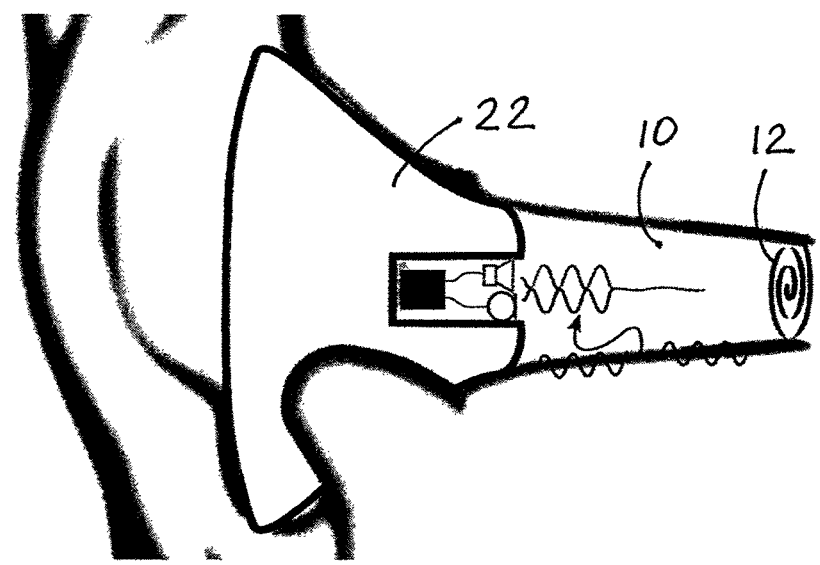
FIG. 5 is a schematic representation of an active noise control (ANC) of occlusion effect, where noise in the ear canal is picked up by an inner-ear microphone (IEM), and a cancellation signal is generated with the loudspeaker (LS)
Figure 6:
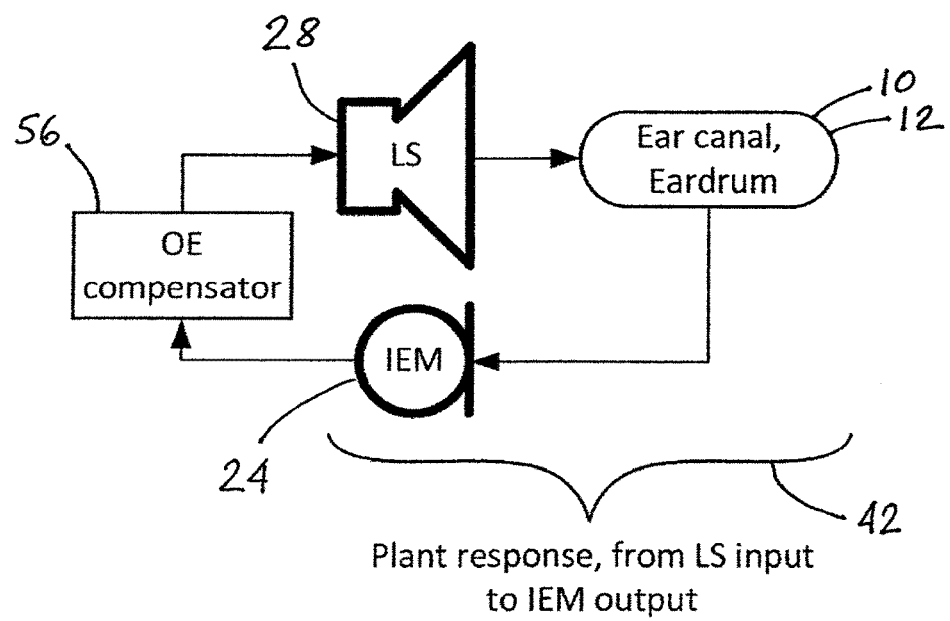
FIG. 6 is a schematic architecture diagram representation of the occlusion effect ANC system and the plant (loudspeaker LS and microphone (IEM) assembly in the occluded ear canal)

The occlusion effect reduction system is based on active noise control (ANC) of the low frequency sound wave which becomes predominant in an occluded ear canal 10. A carefully selected miniature loudspeaker 28 and microphone 24 assembly (referred to as plant) is placed in the ear canal 10, within the HPD 20. A compensator uses the signal picked up by the internal microphone 24 to generate a corresponding anti-noise with the loudspeaker 28. The anti-noise adds up to the noise, in the acoustic domain, and reduces the occlusion effect, as shown in FIG. 5. FIG. 6 shows the architecture of an ANC system.

Figure 7A:
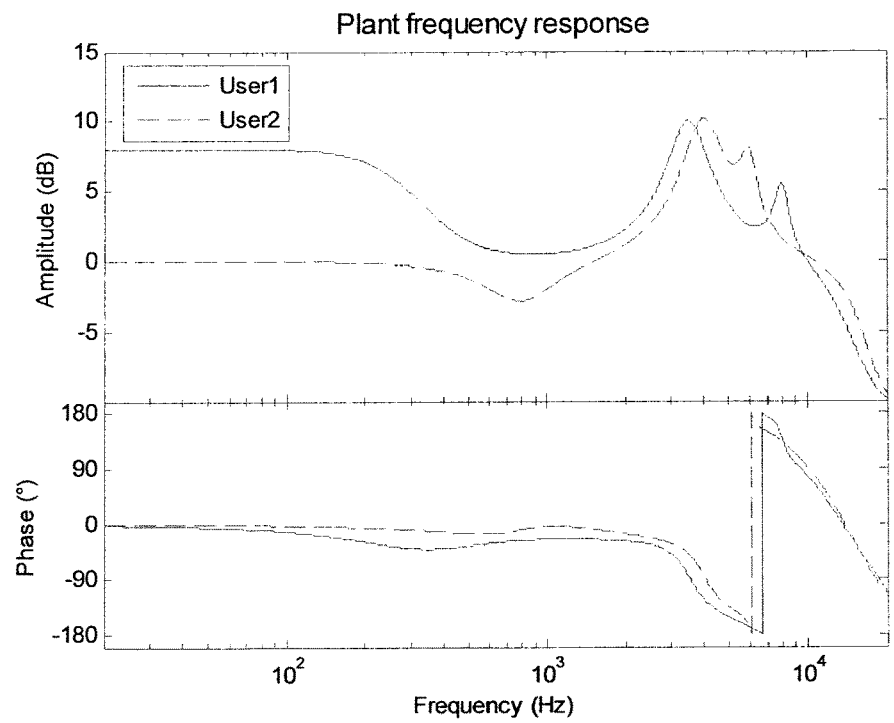
FIGS. 7a-7e is an example of the design of different OE compensator of the present invention to offer similar performance in ear canals that have very different acoustical characteristics.
Figure 7B:
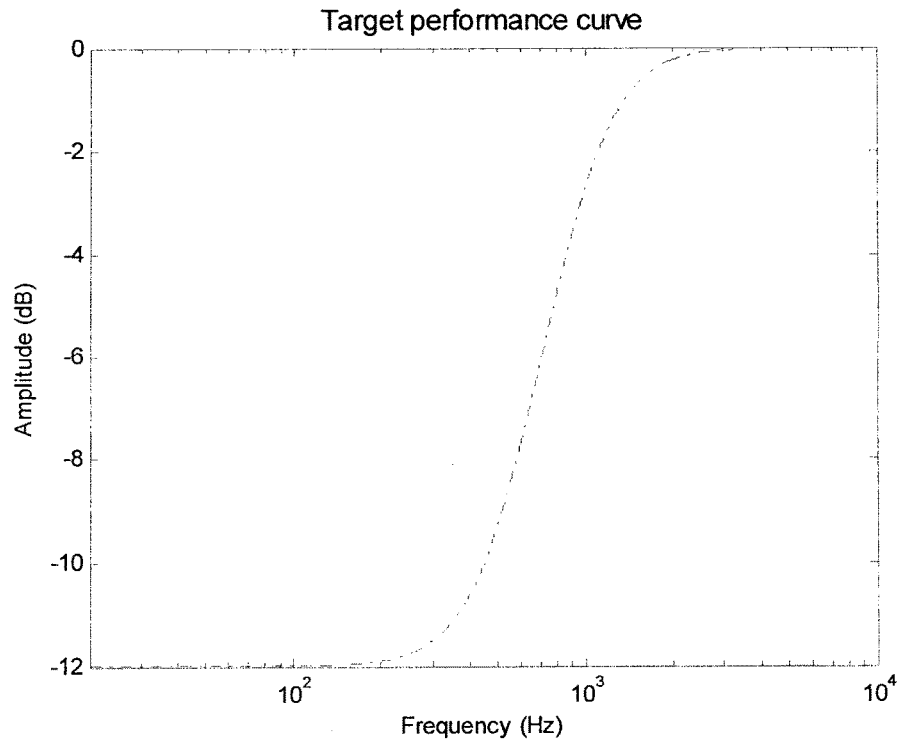
Figure 7C:
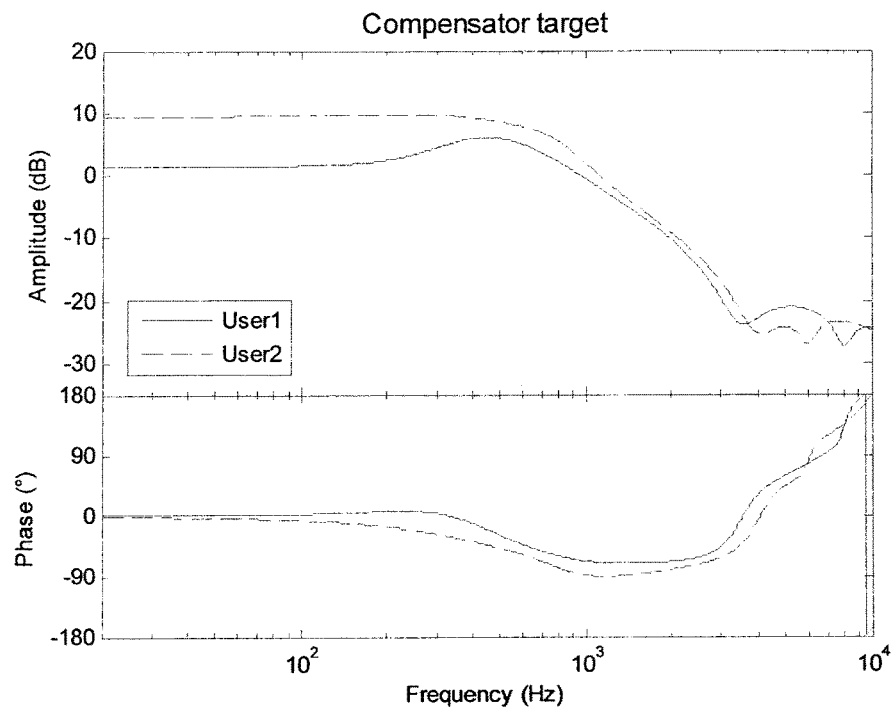
Figure 7D:
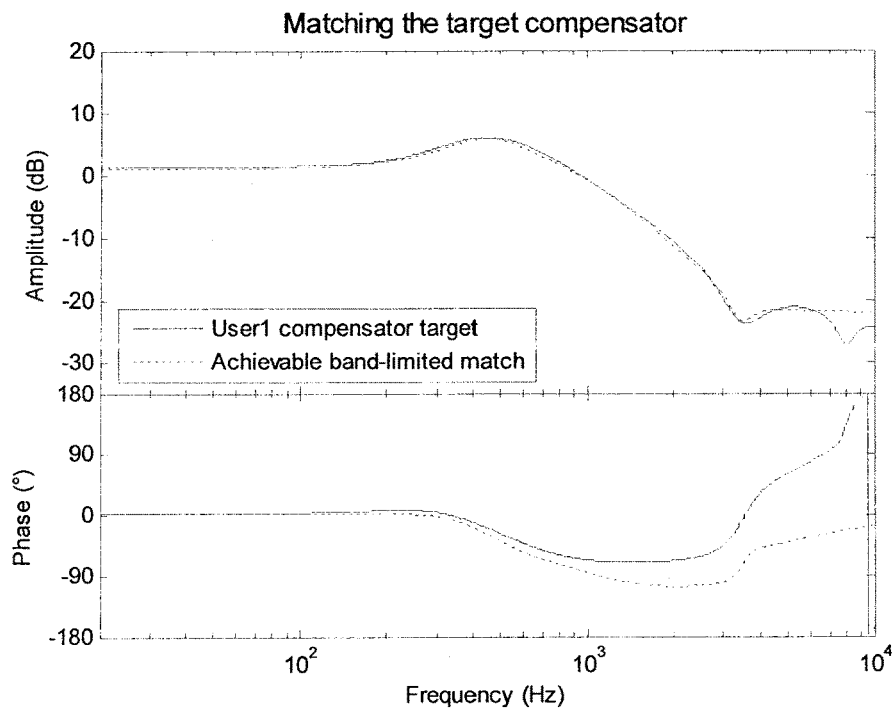
Figure 7E:
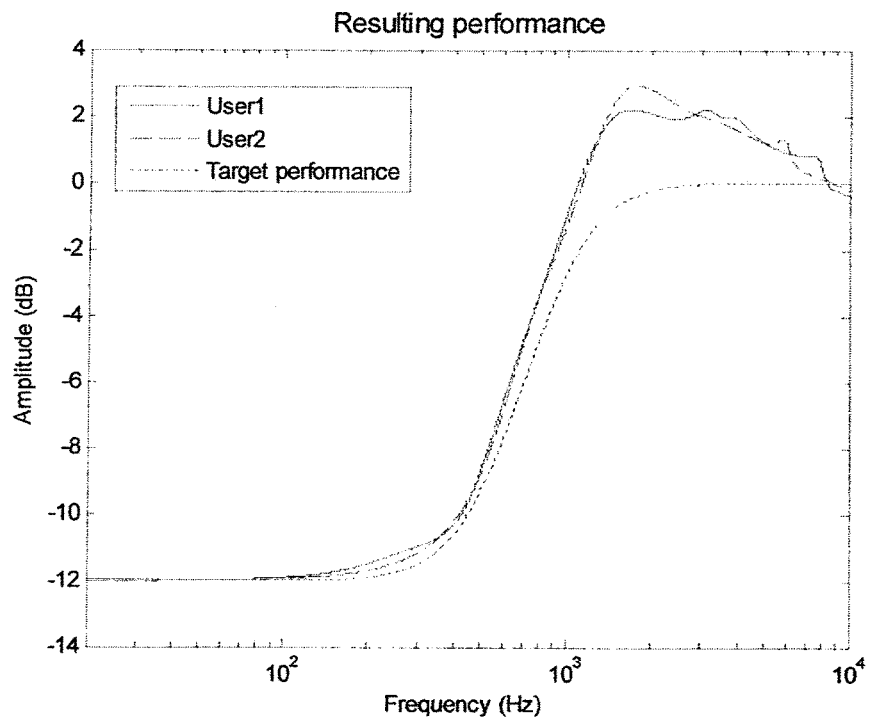

Since the compensator 56 is automatically designed in-situ, taking into account measurements of the user's acoustic characteristics 40 and resulting plant response 42 as discussed above, consistent performance can be achieved over a wide range of user with different characteristics. An example of this is shown on FIGS. 7a-7e. FIG. 7a shows plant responses, the frequency response from the LS input to the IEM input, of the device is inserted in two different ear canals of different users. Variability is observed, in this instance, by different low frequency responses, often depending on the remaining volume of the occluded ear canal and the quality of the acoustic seal between the device and the ear canal, among other factors. Higher frequencies differences are also observed, often a result of the different ear canal length and shapes, among other factors. These frequencies therefore contain the specific acoustic characteristics of the ear canal of the users. Should a fixed OE compensator be used in that case, OE active control performance would vary greatly across these users and their experiences would be completely different. FIG. 7b shows an example target OE active control performance that could be desirable in both cases. FIG. 7c shows the frequency responses of the OE compensators that would result in the target OE active control performance of FIG. 7b for both users. It can be seen that they differ significantly. FIG. 7d shows an example of the OE compensator that resulted from an iterative automatic design, within constraints including stability, that best matches the target OE compensator for user-1 given practical concerns. A similar process (not shown) occurs for user-2. FIG. 7e shows the resulting performance for both users after their respective OE compensators are running in their ear canals. It can be seen that, although the initial plants responses differed greatly, the OE compensator adapted to their acoustic characteristic to provide performance that match the target performance curve and provide both users with similar experiences. It can be noted that small regeneration occurs in the vicinity of 1 kHz to 4 kHz. This is often unavoidable with ANC systems. Allowed regeneration is also an example of a parameter that is taken into account in the iterative automatic design of the OE controller.

The process described above is an example of providing two users having different acoustic characteristics with similar OE active cancellation. Given their preferences and needs, their respective target OE active control performance curve could have been different, but the process would be similar.

As previously mentioned, the target OE active control performance curve 54 is determined by the system mainly as a function of pre-defined realistic performance curves 48, user needs 46, which can be deduced by comparing the low frequency content of the IEM to the OEM, from which their occlusion effect SPL increase can be estimated (OE SPL monitoring 50), as well as user preferences input 46. The automatic design of the OE compensator 56 takes into account this target OE active control performance curve 54, the user (or individual) acoustic characteristics 40 and/or plant response 42, as well as internally defined requirements such as stability in the form of gain and phase margins, maximum allowed regeneration and maximum allowed deviation from the target OE active control performance curve 54. This is depicted on FIG. 4.

A benefit of reducing the occlusion effect and canceling low frequencies inside the ear canal 10 is increased low frequency attenuation relative to the earplug passive attenuation 36. This is discussed in the next section.

Addressing the Isolation Effect

For the isolation effect, an external microphone 26 placed on the outside of the HPD 20 is used to capture the useful signal, transform and reproduce it at variable volume through the internal miniature loudspeaker 28. A passive HPD usually attenuates sound unevenly, letting through more low frequencies than high frequencies. As a first step to flatten the attenuation, low frequencies are reduced inside the ear canal 10 as a consequence of the OE active control.

From this point, an IE filter 60 is designed and inserted between the OEM 26 and the LS 28. This signal path is used to inject a corrected signal that, when acoustically combined with the earplug's maximum passive 36 and active attenuation, results in a uniform attenuation over frequencies of a variable magnitude, theoretically offering a uniform attenuation anywhere from 0 dB to the earplug's maximum attenuation, varying across users and determined by the quality of the acoustic seal between the earplug 22 and the ear canal 10 and the performance of the occlusion effect control. To achieve true uniform attenuation on a given user, it is implied that this IE filter 60 must include ear resonance correction for a uniform perceived attenuation. At this point, uniform attenuation is achieved in dB, but might not be perceived as uniform due to lack of frequency specific loudness correction. To obtain a perceived uniform attenuation and compensate for loudness effect, a filter derived from loudness models 66 can be included in the IE filter 60. Using the outside noise level and the desired attenuation as input parameters, it is possible to account for the shift of perception caused by loudness effects. By doing so, the perceived spectral balance is the same with or without the hearing protection, while the overall loudness is reduced.

The digital signal processor (DSP)or controller 30 housing the filters 56, 60, 72 can measure the sound pressure level outside the HPD 20. It can then either calculate and apply the required attenuation to follow a certain standard resulting in safe residual sound in the ear, or apply a user-defined attenuation level 64. The signals from the IEM 24 and OEM 26 can be compared to iterate, adapt and verify that the attenuation is indeed correct. The complete system architecture required to implement both the occlusion effect reduction and isolation effect compensation system is shown in FIG. 8.

Figure 9:
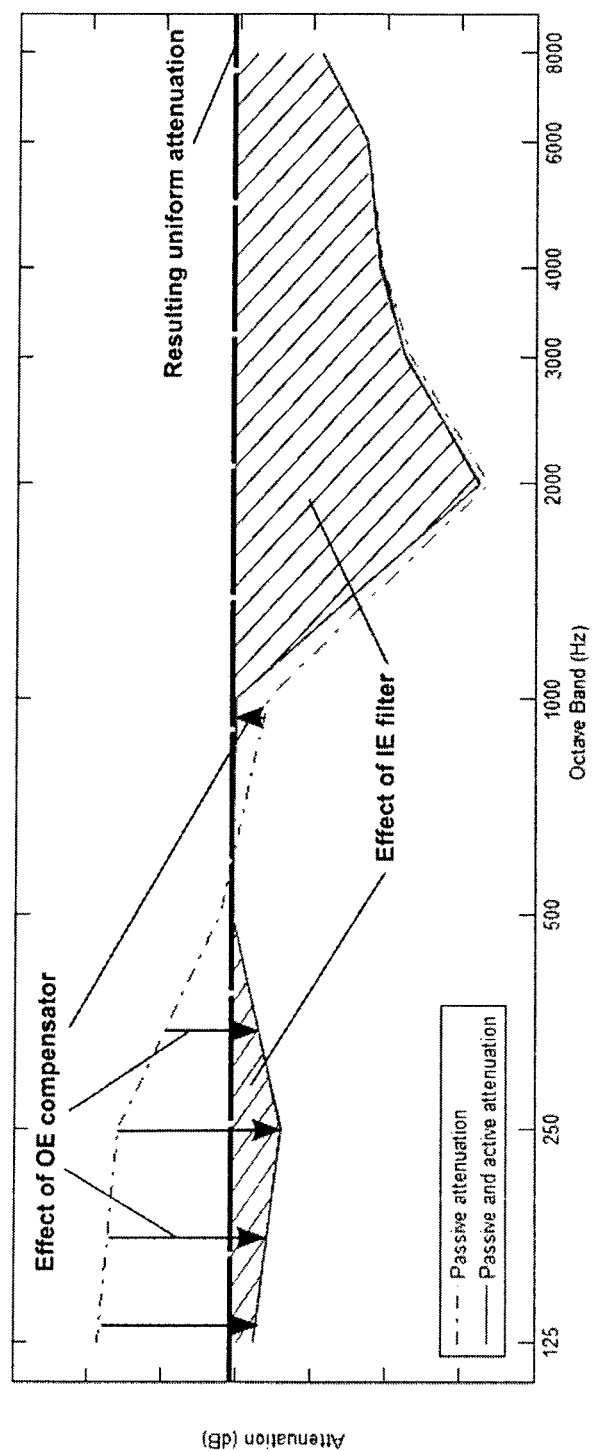
FIG. 9 is a schematic diagram representation of an example of the achieving uniform active attenuation from an uneven passive attenuation, showing the effect of the occlusion effect active noise control (ANC) system, and the isolation effect filter, all summing to uniform attenuation in bold dashed line.

An example of the consequences of the process described above is shown on FIG. 9. It can be seen that the OE active control or compensator 56 increases the effectiveness of the earplug 22 in the areas where it is passively attenuates the least. Given the resulting curve, it is possible to amplify the over-attenuated frequencies to match the attenuation of the least attenuated frequencies, using a DSP. By doing so, higher maximum uniform attenuation are achieved than what was possible without the active system. Another advantage is the adjustability of the attenuation: using the DSP, the level of uniform attenuation can be adjusted by the user depending on his or her needs, preventing over-attenuation that can result in musicians opting out of using HPD. Thus, in the case presented in FIG. 9, uniform attenuation values could range from about 19 dB to any defined lower attenuation bound, such as 6 dB, or even complete bypass of the HPD 20. Notice, that although the resulting attenuation appears to be perfectly uniform in the graph of FIG. 9, it shall be recognized that the process described above can in some cases produce a substantially uniform attenuation without departing from the scope of the present invention.

Although the present invention has been described with a certain degree of particularity, it is to be understood that the disclosure has been made by way of example only and that the present invention is not limited to the features of the embodiments described and illustrated herein, but includes all variations and modifications within the scope of the invention as hereinabove described and hereinafter claimed.

We claim:

1. A hearing protection device for protecting an ear of a user while reducing an occlusion effect and/or an isolation effect induced by the hearing protection device, the device comprising:
    an earpiece for being located into the ear for occluding an ear canal of the ear, said earpiece having an inner-ear microphone (IEM) for being in fluid communication with the occluded ear canal, an outer-ear microphone (OEM) for being in fluid communication with an adjacent environment outside the ear, and a receiver for being in fluid communication with the occluded ear canal; and
    a controller connecting to the inner-ear microphone (IEM) to receive an internal signal therefrom over a predetermined frequency range and to the outer-ear microphone (OEM) to receive an external signal therefrom over the predetermined frequency range, said controller digitally actively processing the internal and external signals taking into account individual acoustic characteristics of the occluded ear canal and sending a processed signal to the receiver, the processed signal and the internal signal producing an actual signal having an actual sound pressure level distribution being uniformly attenuated over the predetermined frequency range relative to a corresponding virtual sound pressure level distribution of a virtual signal that would be heard by the ear of the user with an non-occluded ear, the actual signal compensating for occlusion (OE) and/or isolation (IE) effects of the earpiece.

2. The hearing protection device of claim 1, wherein the controller includes:
    for accounting of the occlusion effect of the earpiece, an OE compensator digitally compensating the internal signal toward a target performance signal curve into an OE compensated signal using the individual acoustic characteristics and an acoustic plant response model including the inner-ear microphone and the receiver, the target performance signal curve being derived from at least one of a pre-defined performance signal curve and a monitoring of an OE induced signal; and
    for accounting of the isolation effect of the earpiece, an IE filter digitally filtering the external signal toward a target system frequency response signal curve into an IE filtered signal using the individual acoustic characteristics and an acoustic system response model including the inner-ear and outer-ear microphones and the receiver, the target system frequency response signal curve being derived from at least one of a pre-defined loudness model curve and a pre-defined passive attenuation signal curve of the earpiece;
    wherein the controller sending the processed signal combining the OE compensated and IE filtered signals to the receiver.

3. The hearing protection device of claim 2, further including:
    a user input item for receiving a first input from the user and connecting to the controller;
    wherein the target performance signal curve being derived from at least one of the pre-defined performance signal curve, the monitoring of the OE induced signal, and the first input.

4. The hearing protection device of claim 3, wherein the user input item is for receiving a second input from the user, the target system frequency response signal curve being derived from at least one of the pre-defined loudness model curve, the pre-defined passive attenuation signal curve of the earpiece, and the second input.

5. The hearing protection device of claim 4, wherein the controller ensures a minimum phase shift of the processed signal relative to the internal signal, and allows maximum gain and phase margins of the processed signal using the first and second inputs from the user.

6. The hearing protection device of claim 4, further including an auxiliary port connecting to the controller and for receiving an auxiliary signal therein to be transmitted to the receiver, and wherein, for accounting of an impact of the auxiliary signal on the actual signal, the controller further includes an auxiliary filter digitally filtering the external signal toward a target auxiliary frequency response signal curve into an auxiliary adjusted signal using the individual acoustic characteristics and an acoustic plant response model, the target auxiliary frequency response signal curve being derived from a pre-defined auxiliary target curve, and wherein the controller sending the processed signal combining the OE compensated, IE filtered and auxiliary adjusted signals to the receiver.

7. The hearing protection device of claim 6, wherein the user input item is for receiving a third input from the user, the target auxiliary frequency response signal curve being derived from at least one of the pre-defined auxiliary target curve and the third input.

8. The hearing protection device of claim 7, wherein the first input from the user is a first tuning factor of an amplitude and/or frequency of the compensated signal so as to allow the user to select a desired amplitude and/or frequency thereof.

9. The hearing protection device of claim 8, wherein the second input from the user is an attenuation level of the filtered signal so as to allow the user to select a desired attenuation thereof.

10. The hearing protection device of claim 9, wherein the third input from the user is an auxiliary attenuation level of the auxiliary adjusted signal so as to allow the user to select a desired attenuation thereof.

11. The hearing protection device of claim 2, wherein at least one of the individual acoustic characteristics and the passive attenuation signal curve of the earpiece being determined from the internal and external signals measured under a plurality of pre-determined test sound environment signals.

12. The hearing protection device of claim 2, wherein at least one of the target performance signal curve and the target system frequency response signal curve is actively modified depending on at least one of the individual acoustic characteristics, the acoustic plant response model, and the acoustic system response model.

13. The hearing protection device of claim 6, wherein at least one of the target performance signal curve, the target system frequency response signal curve, and the target auxiliary frequency response signal curve is actively modified depending on at least one of the individual acoustic characteristics, the acoustic plant response model, and the acoustic system response model.

14. A method for reducing acoustic occlusion (OE) and/or isolation (IE) effects induced by an earpiece located into an ear of a user and occluding an ear canal of the ear, the earpiece having an inner-ear microphone (IEM) for being in fluid communication with the occluded ear canal, an outer-ear microphone (OEM) for being in fluid communication with an adjacent environment outside the ear, and a receiver for being in fluid communication with the occluded ear canal, a controller connects to the internal and outer ear microphones and to the receiver, the method comprising the step of:
actively reducing acoustic occlusion (OE) and/or isolation (IE) effects induced by the earpiece located into the occluded ear canal using the controller sending a actively processed signal to the receiver based on signals received by the internal (IEM) and outer (OEM) ear microphones over a predetermined frequency range and taking into account individual acoustic characteristics of the occluded ear canal, the actively processed signal and the internal signal producing an actual signal having an actual sound pressure level distribution being uniformly attenuated over the predetermined frequency range relative to a corresponding virtual sound pressure level distribution of a virtual signal that would be heard by the ear of the user with an non-occluded ear, the actual signal compensating for occlusion (OE) and/or isolation (IE) effects of the earpiece.

15. The method of claim 14, wherein the step of actively reducing includes actively controlling the occlusion effect (OE) from the earpiece and actively compensating for the isolation effect (IE) induced by the earpiece.

16. The method of claim 15, wherein the controller includes an OE compensator and an IE filter, and wherein the step of actively controlling includes the steps of:
using the OE compensator for accounting of the occlusion effect of the earpiece, digitally compensating the internal signal toward a target performance signal curve into an OE compensated signal using the individual acoustic characteristics and an acoustic plant response model including the inner-ear microphone and the receiver, the target performance signal curve being derived from at least one of a pre-defined performance signal curve and a monitoring of an OE induced signal; and
using the IE filter for accounting of the isolation effect of the earpiece, digitally filtering the external signal toward a target system frequency response signal curve into an IE filtered signal using the individual acoustic characteristics and an acoustic system response model including the inner-ear and outer-ear microphones and the receiver, the target system frequency response signal curve being derived from at least one of a pre-defined loudness model curve and a pre-defined passive attenuation signal curve of the earpiece; the controller sending the processed signal combining the OE compensated and IE filtered signals to the receiver.

17. The method of claim 16, wherein at least one of the target performance signal curve and the target system frequency response signal curve is actively modified depending on at least one of the individual acoustic characteristics, the acoustic plant response model, and the acoustic system response model.

18. The method of claim 16, wherein an auxiliary port for receiving an auxiliary signal therein to be transmitted to the receiver connects to the controller, and wherein the step of actively controlling includes the step of:
using the auxiliary filter for accounting of an impact of the auxiliary signal on the actual signal, the controller further includes an auxiliary filter digitally filtering the external signal toward a target auxiliary frequency response signal curve into an auxiliary adjusted signal using the individual acoustic characteristics and an acoustic plant response model, the target auxiliary frequency response signal curve being derived from a pre-defined auxiliary target curve; the controller sending the processed signal combining the OE compensated, IE filtered and auxiliary adjusted signals to the receiver.

19. The method of claim 18, wherein at least one of the target performance signal curve, the target system frequency response signal curve, and the target auxiliary frequency response signal curve is actively modified depending on at least one of the individual acoustic characteristics, the acoustic plant response model, and the acoustic system response model.

20. The method of claim 18, wherein a user input item for receiving at least one input from the user connects to the controller, and wherein at least one of the target performance signal curve, the target system frequency response signal curve, and the target auxiliary frequency response signal curve is further derived from the at least one input.

21. The method of claim 20, wherein the step of actively controlling includes the step of:
ensuring a minimum phase shift of the processed signal relative to the internal signal, and allowing maximum gain and phase margins of the processed signal using the at least one input from the user.

22. The method of claim 16, further including, before the step of actively controlling, the step of:
determining at least one of the individual acoustic characteristics and the passive attenuation signal curve of the earpiece from the internal and external signals measured under a plurality of pre-determined test sound environment signals.

* * * * *